United States Patent
Zavrel et al.

(10) Patent No.: US 9,988,658 B2
(45) Date of Patent: Jun. 5, 2018

(54) PROCESS FOR THE HYDROLYSIS OF BIOMASS

(71) Applicant: Clariant International Ltd., Muttenz (CH)

(72) Inventors: Michael Zavrel, Olching (DE); Danielle Dennewald, Munich (DE); Sandra Schuetze, Gmund am Tegernsee (DE); Marcus Verhuelsdonk, Rosenheim (DE); Markus Jakob, Munich (DE)

(73) Assignee: CLARIANT INTERNATIONAL LTD., Muttenz (CH)

( * ) Notice: Subject to any disclaimer, the term of this patent is extended or adjusted under 35 U.S.C. 154(b) by 0 days. days.

(21) Appl. No.: 14/917,943

(22) PCT Filed: Oct. 15, 2014

(86) PCT No.: PCT/EP2014/072147
§ 371 (c)(1),
(2) Date: Mar. 9, 2016

(87) PCT Pub. No.: WO2015/055731
PCT Pub. Date: Apr. 23, 2015

(65) Prior Publication Data
US 2016/0215313 A1   Jul. 28, 2016

(30) Foreign Application Priority Data
Oct. 18, 2013 (EP) .................................... 13004990

(51) Int. Cl.
| | |
|---|---|
| *C12P 19/14* | (2006.01) |
| *C12P 7/14* | (2006.01) |
| *C12P 19/02* | (2006.01) |
| *C13B 20/16* | (2011.01) |
| *C13K 1/02* | (2006.01) |

(52) U.S. Cl.
CPC ............... *C12P 19/14* (2013.01); *C12P 7/14* (2013.01); *C12P 19/02* (2013.01); *C13B 20/165* (2013.01); *C13K 1/02* (2013.01)

(58) Field of Classification Search
CPC .. C12P 19/14; C12P 7/14; C12P 19/02; C13K 1/02; C13B 20/165

USPC .......................................................... 435/105
See application file for complete search history.

(56) References Cited

U.S. PATENT DOCUMENTS

| | | | | |
|---|---|---|---|---|
| 5,256,297 | A | * 10/1993 | Feimer ................. | B01D 61/142 210/195.2 |
| 2012/0135475 | A1 | * 5/2012 | Koltermann ............ | C12P 19/02 435/99 |

FOREIGN PATENT DOCUMENTS

| | | |
|---|---|---|
| EP | 0737753 A1 | 10/1996 |
| EP | 2256208 A1 | 12/2010 |
| EP | 2650384 A1 | 10/2013 |
| WO | 2013105033 A1 | 7/2013 |

OTHER PUBLICATIONS

Beldman et al.; "Application of cellulase and pectinase from fungal origin for the liquefaction and saccharification of biomass", Enzyme Microb. Technol., 1984, vol. 6, November, p. 503-507; XP 023678124.

Jing et al.; "Inhibition Performance of Lignocellulose Degradation Products on Industrial Cellulase Enzymes During Cellulose Hyddrolysis" Appl. Biochem Biotechnol. 2009, 159(3): 696-707.

Tjerneld, F., et al.; "Enzymes Recycling in Cellulose Hydrolysis by Combinsd Use of Aqueous Two-Phase Systems and Ultrafiltration", Biotechnology and Bioengineering Symp., John Wiley & Sons US vol. 17, No. 15; XP 009040364.

Tanaka, M., et al.; "Removal of Lignin and Reuse of Cellulases for Continuous Saccharification of Lignocelluloses", Biotechnology and Bioengineering, vol. 32, pp. 897-902; XP 002096253.

* cited by examiner

*Primary Examiner* — Scott Long
*Assistant Examiner* — Paul C Martin
(74) *Attorney, Agent, or Firm* — Gianna Julian-Arnold; Saul Ewing Arnstein & Lehr LLP

(57) ABSTRACT

The present invention is directed to a process for the hydrolysis of biomass as well as the saccharide-containing permeate product and the protein-containing product produced by this process. In a further aspect, the present invention is directed to a process for the production of organic compounds from the saccharide-containing product. In an additional aspect the present invention is directed to the use of the protein-containing product for the production of a fermentation medium.

11 Claims, 5 Drawing Sheets

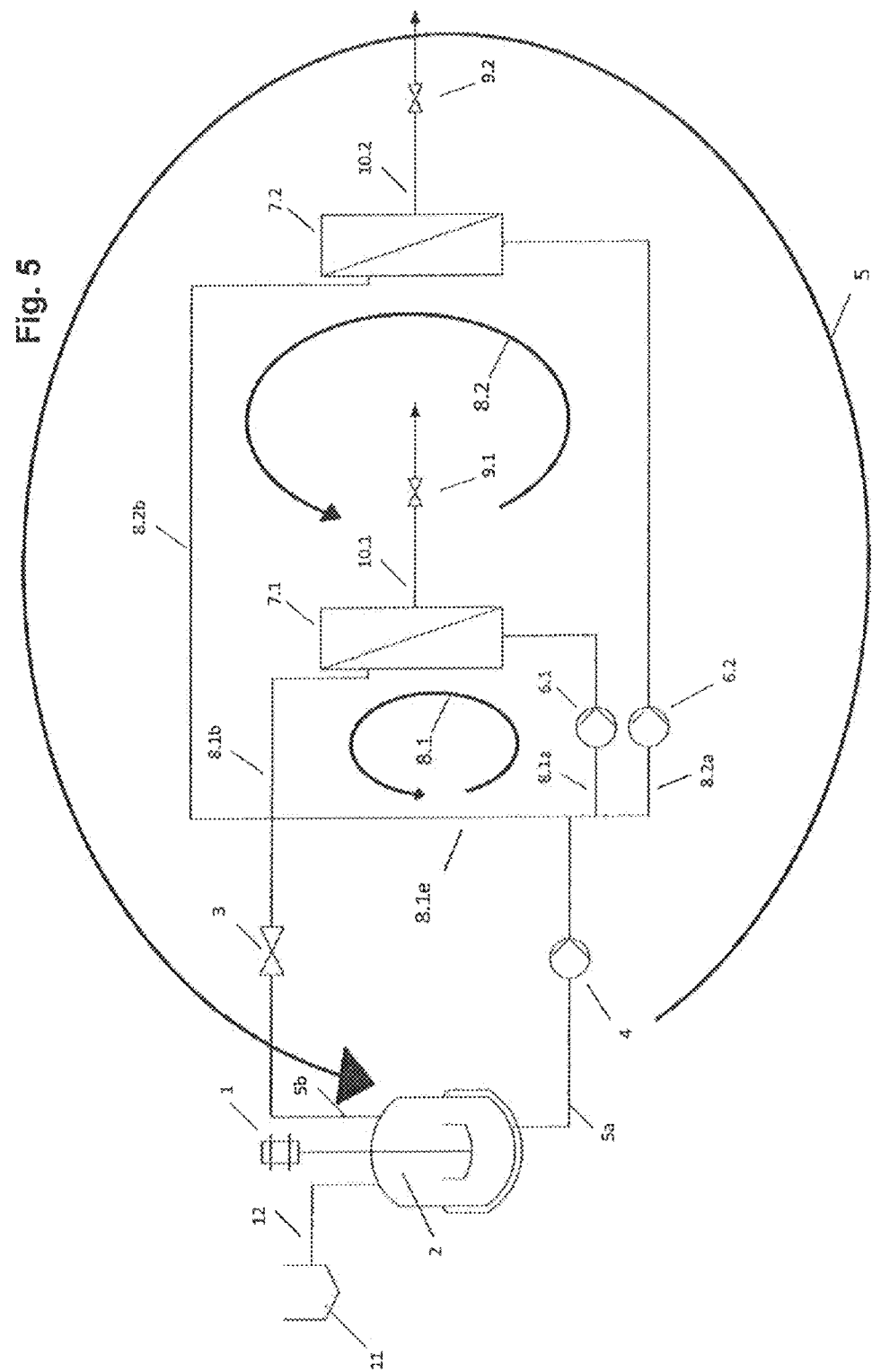

PROCESS FOR THE HYDROLYSIS OF BIOMASS

CROSS REFERENCE TO RELATED APPLICATIONS

This application claims the priority of PCT/EP2014/072147, filed on 15 Oct. 2014, which claims priority to European Patent Application No. 13004990.1, filed 18 Oct. 2013, the entire contents of each of which are hereby incorporated in total by reference.

The present invention is directed to a process for the hydrolysis of biomass as well as the saccharide-containing permeate-product and the protein-containing product produced by this process. In a further aspect, the present invention is directed to a process for producing organic compounds from the saccharide-containing permeate. In an additional aspect the present invention is directed to the use of the protein-containing product for the production of a fermentation medium.

Biomass originating from crops such as sugar beet, corn, straw and other saccharide- or polysaccharide- and protein-containing material are valuable sources not only for refined saccharides such as monomeric or dimeric sugars, but also for other components such as amino acids, proteins and minerals.

There are processes within the state of the art for hydrolyzing and separating and refining single components such as sugars from sugar beets. In such processes, however, other valuable components such as cell wall compounds and proteins are discarded after extraction and refining of monomeric and dimeric sugars such as sucrose. Within a well established process sugar is removed from e.g. sugar beet by extracting sliced sugar beet with hot water in a continuous counter-flow process. Usually, such process requires the addition of further agents such as CaO in an amount of around 1 to 3 kg of CaO per 100 kg of sugar beet. Products of this process are the sugar solution, called raw juice, and the so-called beet pulp, the latter being dried in a pulp dryer. The raw juice is further purified and filtrated, and subsequently concentrated to yield thick juice (65 to 70% dry matter content), or, after crystallization, to yield refined sugar. The elevated temperature and pH conditions during this process cause the destruction of a crucial amount of monosaccharides contained in the solution. Further, due to the decomposition of nitrogen compounds ammonia is produced. In addition, the so called beet-pulp still contains not only the majority of proteins of the sugar beet but also the majority of polysaccharides such as cellulose, hemicellulose and pectin. According to the German Zuckerverband, in 2011/2012, a total of 4.266.670 t sugar was produced in Germany (given as "t Weißzuckerwert") corresponding to 1.907.302 t Schnitzel ("remnant") (indicated as "t Trockenschnitzelwert"). As a consequence, roughly 0.45 t remnant per t sugar arise as waste material.

One advanced process is described within the EP 0737753 A1 which discloses a process for the production of sucrose from raw juice of sugar beet through concentration under vacuum by feeding the juice over one or more evaporators with concentration in counter-current and with evaporation of the more diluted juice at lower temperature. Even though several improvements have been made to the basic process, it is obvious that the main drawbacks such as high consumption of energy and the high amount of undifferentiated remnants are problematic.

Another process for producing fermentation syrups from sugar-beet pulp and potato fibre relating to the use of enzymes such as cellulase and pectinase is described by Beldman et al. (Enzyme Microb. Technol. 1984, vol. 6, November, p. 503-507). It was, however, found that part of the enzyme activity was lost during the process. Moreover, a very high enzyme to substrate ratio of 8.44% (g/g) was applied which makes the process non-economic. It is not mentioned how the required enzyme concentration can be minimized. Furthermore, two vessels are required which is expensive. Another process which uses enzymes for beet-pulp hydrolysis is described in EP 2 256 208 A1, however, the resulting product still contains solid-components of the sugar beet and there is no further separation of other valuable components.

Further processes for the liberation of monomeric sugars and sucrose from cellulose-, pectin- and hemicellulose-containing biomass such as sugar beet using chemical treatment have been described within the state of the art. For example unselective processes such as sulphuric acid treatment can be used to hydrolyze sugar beet; however such treatment is inefficient at low temperatures. At higher temperatures (e.g. dilute acid steam pretreatment at 200-250° C.) it leads to inhibitory components such as hydroxymethylfurfural (HMF) or furfural that render a subsequent fermentation process problematic (Jing et al., 2009 Appl Biochem Biotechnol, 2009; 159(3): 696-707).

Thus, there is a need for an improved process for the hydrolysis of biomass in that not only a high amount of monomeric and dimeric sugars may be obtained but also other valuable components of the biomass can be retained and separated for special purposes. Further, there is a need for an energy-efficient and economical process. In addition, there is the need for a process enabling the hydrolysis of biomass applying a reduced amount of hydrolytic enzymes. Finally, there is a need for a process for obtaining higher yields of monomeric and dimeric sugars from biomass.

It is thus the object underlying the present invention to provide a process for hydrolyzing biomass which does not show any of the disadvantages of the processes known within the state of the art.

In a first aspect, the invention thus provides a process for hydrolyzing biomass comprising the steps of
  a) Contacting the biomass with an enzyme-composition containing at least one enzyme selected from the class of hydrolases in a vessel;
  b) Eliminating a part of said biomass;
  c) Subjecting said part of biomass to a filtration, and removing the permeate;
  d) Backfeeding of at least part of the filtrated biomass to the vessel;
  e) Optionally addition of an amount of liquid corresponding to the amount removed by filtration according to step c);
wherein step b) and step c) of the process are carried out in distinct circuits.

The term "biomass" as used within the present invention refers to any type of biomass known to a person skilled in the art as suitable for the inventive process. Particularly preferred is biomass of plant-origin. Within a further preferred embodiment, the initial dry matter content of the biomass is selected from 5 to 40 wt.-%, more preferred from 15 to 30 wt.-%. The term "dry matter" (d.m.) refers to the mass to biomass ratio determined after water and other volatile compounds have been removed from fresh tissue using an IR-balance. It is thereby particularly preferred to select a biomass whereby its dry matter contains at least 25 wt.-% of saccharides such as monomeric sugars, dimeric sugars and oligosaccharides and/or polysaccharides, more preferred at least 40 wt.-%, particularly preferred at least 60 wt.-%, further preferred at least 80 wt.-% of saccharides such as monomeric sugars, dimeric sugars and oligosaccharides and/or polysaccharides. Further, any mixtures of suitable biomasses are to be included within the term "biomass".

Particularly preferred biomass is selected from "sugar beet biomass" and/or "sugar cane biomass" and/or "lignocellulose biomass". The term "sugar beet biomass" refers to the complete and unprocessed root tissue of *Beta vulgaris* including the outer peel and the internal pulp. Dry tissue of *Beta vulgaris* contains 80% wt.-% soluble sucrose, while beet pulp contains approximately 7% pectin, 7% cellulose and 7% hemicellulose, 17% arabinose, 20% glucose and 3.5% fructose and 10% proteins, all relative to the dry matter (d.m.) of the biomass. The term "sugar beet biomass" further comprises sugar beet pulp (sugar beet chips).

The term "sugar cane biomass" refers to the complete and unprocessed stalks of *Saccharum* sp. including the outer peel and the internal pulp. Dry tissue of *Saccharum* sp. contains 80% wt.-% soluble sucrose, while dry cane bagasse is made up of approximately 70% polymeric sugars, including 45% cellulose, 23% lignin and 25% hemicellulose primarily in the form of xylan all relative to the dry matter (d.m.) of the biomass. The term "sugar cane biomass" further comprises sugar cane pressed cake (bagasse).

The term "lignocellulose biomass" refers to residue-, waste- and/or by-products from forestry and agriculture, the food-processing and paper industry and communal waste. In particular, the term "lignocellulose biomass" as used within the present invention includes grain straw and/or spelt (such as wheat, rye, barley, oats), maize straw, stover and/or spindles, grasses such as *Sericea lespedeza*, switchgrass (*Panicum virgatum*), Napier grass (*Miscanthus*; China reed), Sudan grass (*Sorghum sudananse, Sorghum drummondi*), *Arundo donax*, barks, wood, wood residues, wood chips and/or wood chippings, fruit pulp and agave residues.

Further biomass suitable for the process are manure from stables, herbaceous materials, coffee grinds and waste from oil mills such as rapeseed pressed cake and sewage from mills, paper-making stock and waste water from paper mills, waste paper, vegetable and fruit leftovers.

Within a preferred embodiment of the process of the present invention, the biomass is selected from cellulose, hemicellulose and/or lignin-containing biomass.

Within a particularly preferred embodiment of the process of the present invention the biomass is selected from sugar beet, sugar cane, straw, corn, wood, oilseed and mixtures thereof.

Within another particularly preferred embodiment of the process of the present invention the biomass is lignocellulosic biomass from agricultural residues, such as wheat straw, sugar cane bagasse, sugar cane leaves and stalks, and/or maize straw and stover.

The term "hydrolysis" as used within the present invention is to be understood as depolymerization of a polymer by a hydrolysis reaction. Hydrolysis reaction is to be understood as the cleavage of chemical bonds by the addition of water. One way to perform hydrolysis technically is to add hydrolase enzymes to the biomass.

Preferably due to the to the process for the hydrolysis of biomass according to the present invention, saccharides are obtained from the biomass material, wherein it is particularly preferred that at least 50 wt.-% of the saccharides obtained are in the form of monomeric and dimeric sugars, preferably at least 65 wt.-%, more preferred at least 75 wt.-%, also preferred at least 85 wt.-% and most preferred 99 wt.-% all relative to the dry matter (d.m.) of the biomass. It is further possible to obtain of amino acids, oligopeptides, oligosaccharides and/or proteins from the biomass material when applying the process for the hydrolysis of biomass according to the present invention.

The biomass is preferably washed prior to subjecting it to the enzymatic treatment, and washing water is removed prior to further processing. Moreover, it is preferred to provide the biomass in particulate form e.g, by cutting, milling, grinding, shearing, shear-dispersing, chopping, dispersing and/or blending the biomass prior to step (a).

It is a particular advantage of the process for the hydrolysis of biomass that also the application of relatively large biomass particles will still achieve favorable results. The size of the biomass particles is preferably such that at least 90 wt.-% of the particles have a maximum length of 200 mm, more preferred 100 mm, even more preferred 50 mm and most preferred 25. It is further preferred that the size of the biomass particles is preferably such that at least 95 wt.-% of the particles have a maximum length of 200 mm, more preferred of 100 mm, even more preferred of 50 mm and most preferred of 25 mm.

Within step a) of the process for the hydrolysis of biomass, the biomass is contacted with an enzyme-composition containing at least one enzyme selected from the class of hydrolases.

The term "contacting" as used within the process for the hydrolysis of biomass comprises any kind of contacting of biomass with an enzyme composition known to a person skilled in the art as suitable for the inventive process. Within a preferred embodiment, the "contacting" of the biomass with the enzyme composition is carried out by adding the enzyme composition to the biomass. Further, it is particularly preferred that the addition of the enzyme composition is followed by or carried out concurrently with a mixing of the enzyme composition and the biomass.

The term "enzyme composition" as used within the present invention of the process for the hydrolysis of biomass refers to any composition comprising at least one enzyme selected from the class of hydrolases. The at least one enzyme selected from the class of hydrolases amounts preferably to from 1 to 99.99 wt.-% (relative to the weight of the enzyme composition), further preferred to from 5 to 99 wt.-%, particularly preferred to from 10 to 95 wt.-% and most preferred to from 20 to 90 wt.-% and may further contain at least one enzyme selected from the class of lyases. Within embodiments of the present invention, wherein the enzyme-composition contains at least one enzyme selected from the class of lyases, the at least one enzyme selected from the class of hydrolases preferably amounts to from 0.01 to 50 wt.-% (relative to the weight of the enzyme composition), preferred to from 0.05 to 20 wt.-%, more preferred to from 0.08 to 5 wt.-% and most preferred to from 0.1 to 1 wt.-%.

Within a preferred embodiment of the process of the present invention for the hydrolysis of biomass, the enzyme composition contains cellulases, hemicellulases and/or pectinases.

Within a further preferred embodiment of the process for the hydrolysis of biomass the enzyme composition further contains at least one enzyme selected from pectinmethylesterases, rhamnogalacturonases, 1,3-/1,6-beta-D-glucanases and/or xylanases.

Within a more preferred embodiment of the process for the hydrolysis of biomass the enzyme composition contains cellulases, hemicellulases and pectinases and at least one enzyme selected from pectinmethylesterases, rhamnogalacturonases, 1,3-/1,6-beta-D-glucanases and/or xylanases.

Within a particularly preferred embodiment of the process for the hydrolysis of biomass the enzyme composition contains cellobiohydrolases (CBH) (EC 3.2.1.-), endo-1,4-β-glucanases (EG) (EC 3.2.1.4).), endo-xylanases (EC 3.2.1.8), β-xylosidases (EC 3.2.1.37), polygalacturonases (EC 3.2.1.15, 67, 82; GH28) and pectin/pectate lyases (EC 4.2.2.2, 6, 9, 10). Within a further particularly preferred embodiment this enzyme composition further contains one or more enzymes selected from β-glucosidase (EC 3.2.1.4), glycoside hydrolase 61 (GH61 and CBM33), β-glucanases (EC 3.2.1.-), acetylxylan esterase (EC 3.1.1.72), acetylgalactan esterase (3.1.1.6)), α-arabinopyranosidase (3.2.1.-), α-galactosidase (EC 3.2.1.22), β-galactosidase (EC 3.2.1.23), α-glucuronidases (EC 3.2.1.139), β-mannase (EC 3.2.1.78), pectin methyl esterase (EC 3.1.1.11), pectin acetyl esterase (EC 3.1.1.-), rhamnogalacturonase (EC 3.2.1.-; G1128), rhamnogalacturonan acetylesterase (EC 3.1.1.86), rhamnogalacturonan endolyase (EC 4.2.2.23), rhamnogalacturonan lyase (EC 4.2.2.-) and β-mannosidases (EC 3.2.1.25).

The terms "cellulases", "hemicellulases" and "pectinases" as used within the present invention of the process for the hydrolysis of biomass refer to any blend of enzymes which is involved in the hydrolytic degradation (depolymerization) of polymeric cellulose, hemicellulose and/or pectin to monomeric sugars. As used herein, the terms "cellulases", "hemicellulases" and "pectinases" refer to both naturally occurring and non-naturally occurring blends that include a plurality of enzymes as produced by an organism, for example a filamentous fungus. "Cellulases", "hemicellulases" and "pectinases" are preferably derived from fungi such as members of the subdivision Eumycota and Oomycota, including but are not limited to the following genera: *Aspergillus, Acremonium, Aureobasidium, Beauveria, Cephalosporium, Ceriporiopsis, Chaetomium, Chrysosporium, Claviceps, Cochiobolus, Cryptococcus, Cyathus, Endothia, Endothia mucor, Fusarium, Gilocladium, Humicola, Magnaporthe, Myceliophthora, Myrothecium, Mucor, Neurospora, Phanerochaete, Podospora, Paecilomyces, Pyricularia, Rhizomucor, Rhizopus, Schizophylum, Stagonospora, Talarornyces, Trichoderma, Thermomyces, Thermoascus, Thielavia, Tolypocladium, Trichophyton,* and *Trametes*. In a preferred implementation, the filamentous fungus is a *Trichoderma* species.

Within a preferred embodiment of the enzyme-composition the cellulases and/or pectinases are from a fungal source. Within a particularly preferred embodiment of the enzyme-composition, this fungal source is *Trichoderma reesei*.

The term "blend of enzymes" preferably refers to a blend of enzymes secreted from one single or more microbial sources. In some embodiments, enzymes for use in these blend(s) of enzymes can be prepared from one or more naturally occurring or engineered strains of filamentous fungi. Preferred strains are listed above. The desired ratio of enzyme components within the final blend(s) can be achieved by altering the relative amount of enzyme in the final blend e.g. by supplementation of purified or partially purified enzyme(s).

As used within the process for the hydrolysis of biomass, the term "cellulase" refers to any enzyme capable of hydrolyzing cellulose polymers to shorter oligomers and/or glucose. Cellulases preferred within the enzyme composition include cellobiohydrolases (CBH) (EC 3.2.1.-), endo-1,4-β-glucanases (EG) (EC 3.2.1.4).), β-glucosidase (EC 3.2.1.4), cellobiose hydrolase (EC 3.2.1.21), glycoside hydrolase 61 (GH61 and CBM33), Expansin, Swollenin, Loosinin and CIP Proteins (EC 3.1.1.-; CE15).

Within a preferred enzyme-composition the term "cellulases" comprises at least one enzyme selected from the group of CBH1, CBH2, EG1, EG2, EG4, xylanases and xylosidases.

As used within the process for the hydrolysis of biomass, the term "hemicellulase" refers to any enzyme capable of degrading or supporting the degradation of hemicellulose.

Hemicellulases preferred within the enzyme composition include β-glucanases (EC 3.2.1.), endo-xylanases (EC 3.2.1.8), β-xylosidases (EC 3.2.1.37), acetylxylan esterase (EC 3.1,1.72), acetylgalactan esterase (3.1.1.6), acetyl mannan esterase, feruloyl esterase (EC 3.1.1.73), glucuronoyl esterase (EC 3.1.1,), α-L-arabinafuranosidase (EC 3.2.1.55), α-arabinopyranosidase (3.2.1.), α-galactosidase (EC 3.2.1.22), β-galactosidase (EC 3.2.1.23), α-glucuronidases (EC 3.2.1.139), β-mannase (EC 3.2.1.78), β-mannosidases (EC 3.2.1.25), mannan 1,4-mannobiosidase (EC 3.2.1.100), arabinogalactan endo-beta-1,4-galactanase (EC 3.2.1.89), endo-beta-1,3-galactanase (EC 3.2.1.90), galactan endo-beta-1,3-galactanase (EC 3.2.1.181, glucuronoarabinoxylan endo-1,4-beta-xylanase (EC 3.2.1.136), alpha-L-fucosidase (EC 3.2.1.51), coniferin beta-glucosidase (EC 3.2.1.126), xyloglucan hydrolases (EC 3.2.1.150, 151, 155), xylan α-1, 2-glucuronosidase (EC 3.2.1.131), endo-xylogalacturonan hydrolase (EC 3.2.1.-; GH28), α-amylase (EC 3.2.1.1), glucan 1,4-α-glucosidase (EC 3.2.1.3), galactan 1,3-galactosidase (GH43), 1,4,-endogalactanase (EC 3.5,1.89; GH53), α-rhamnosidase (EC 3.2.1.40), β-rhamnosidase (EC 3.2.1.43), lignin peroxidase (EC 1.11.1.14), Mn peroxidase (EC 1.11.1.13), aryl-alcohol oxidase (EC 1.1.3.7), glyoxal oxidase (EC 1.1.3.), carbohydrate oxidases (EC 1.1.3.4, 9, 10) and cellobiose dehydrogenase (EC 1,1.99.18).

As used within the process for the hydrolysis of biomass, the term "pectinase" refers to any enzyme capable of degrading or supporting the degradation of pectin. Pectinases preferred within the enzyme composition include polygalacturonases (EC 3.2.1.15, 67, 82; GH28), pectin/pectate lyases (EC 4.2.2.2, 6, 9, 10), pectin methyl esterase (EC 3.1.1.11), pectin acetyl esterase (EC 3.1.1.), rhamnogalacturonase (EC 3.2.1.; GH28), rhamnogalacturonan acetylesterase (EC 3.1.1.86), rhamnogalacturonan endolyase (EC 4.2.2.23), rhamnogalacturonan lyase (EC 4.2.2.), rhamnogalacturonan galacturonohydrolase (EC 3.2.1.), xylogalacturonan hydrolase (EC 3.2.1.), pectin methylesterase (EC 3.1.1.11), beta-arabinopyranosidase (EC 3.2.1.55), beta-1,4-galactanase (EC 3.2.1.89), beta-1,3-galactanase (EC 3.2.1.90), beta-galactosidase (EC 3,2.1.23), alpha-galactosidase (EC 3.2.1.22), feruloyl acetyl esterase (EC 3.1.1.-), alpha-fucosidase (EC 3.2.1.51), (beta-fucosidase) (EC 3.2.1.38), beta-apiosidase (EC 3.2.1.-), alpha-rhamnosidase (EC 3.2.1.40), beta-rhamnosidase (EC 3.2.1.43), alpha-arabinopyranosidase (EC 3.2.1.), beta-glucuronidase (EC 3.2.1.31), alpha-glucuronidase (EC 3.2.1.139), beta-xylosidase (EC 3.2.1.37) and alpha-xylosidase (EC 3.2.1.x).

Within a preferred enzyme-composition the term "pectinases" comprises at least one pectinase selected from the group of pectinesterases, polygalacturonases, pectat lyases, pectin lyases, xylogalacturonases, mannosidase, and rhamnogalacturonase.

The term "pectinmethylesterase" refers to an enzyme of the E.C. 3.1.1.11 class, which catalyses the hydrolysis of methyl substituents from modified polygalacturonan backbone.

The term "rhamnogalacturonase" refers to an enzyme of the E.C. 3.2.1 class, which catalyses the hydrolysis of rhamnose substituents of polygalacturonan backbone.

The term "1,3-/1,6-D-glucanase" refers to an enzyme of the E.C. 3.2.1 class, which catalyses the hydrolysis of hexose substituents of 1,3-/1,6-modified sugar polymers.

The term "xylanase" refers to an enzyme of the B.C. class 3.2.1.8, which catalyses the random hydrolysis of polymeric xylan, polymeric pectin, or hemicellulose containing xylose residues resulting in the formation of xylose-containing sugar oligomers and/or monomeric xylose residues.

The term "lyase" refers any enzyme that catalyzes the breaking of various chemical bonds by means other than hydrolysis and oxidation, often forming a new double bond or a new ring structure.

The enzymes referenced within the present invention of the process for the hydrolysis of biomass are classified according nomenclatures that are either based on the International Union of Biochemistry and Molecular Biology's Enzyme Nomenclature and Classification (http://www.chem.qmul.ac.uldiubmbienzyme/) or on Carbohydrate-Active EnZYmes (http://www.cazy.orgt) database.

The term "activity" of an enzyme as used within the present invention of the process for the hydrolysis of biomass refers to the catalytic activity of the enzyme under appropriate conditions under which the enzyme serves as a protein catalyst, which converts specific polymeric or artificial substrates to specific oligomeric or monomeric products. In this context the term "appropriate conditions" is well known to and applicable by a person skilled in the art.

The enzymes may be employed in varied relative proportions in a given mixture.

In a preferred embodiment, step (a) of the process for the hydrolysis of biomass is carried out for a time sufficient to hydrolyze at least 20 wt.-%, preferably at least 30 wt.-%, more preferred at least 50 wt.-% and most preferred at least 60 wt.-% of the biomass. Within a further preferred embodiment of the process of the present invention, step (a) is carried out for a time sufficient to hydrolyze from 10 to 100 wt.-%, preferably from 50 to 99.5 wt.-% of the hydrolysable compounds of the biomass. Within the present invention, the term "hydrolyze" is to be understood as the hydrolytic conversion of insoluble polymeric components of the biomass to soluble monomeric, dimeric and/or oligomeric compounds by chemical, physical, and/or enzymatic processes such as hydrolysis.

Within a particularly preferred embodiment, step (a) of the process for the hydrolysis of biomass is carried out for 1 minute to 100 hours, more preferred for 10 minutes to 80 hours, particularly preferred for 30 minutes to 40 hours, even more preferred for 1 hour to 30 hours also particularly preferred from 2 hours to 20 hours.

Within a further preferred embodiment, step (a) of the process for the hydrolysis of biomass is carried out until the content of remaining insoluble solids is less than 30 wt.-%, preferably less than 20 wt.-%, even more preferred less than 12.5 wt.-%. In a further preferred embodiment, step (a) of the process for the hydrolysis of biomass is carried out until the content of remaining insoluble solids is from 5 to 30 wt.-%, preferably from 10 to 20 wt.-% and most preferred from 12.5 to 17.5 wt.-%.

Within another preferred embodiment of the present invention of the process for the hydrolysis of biomass, step (a) is carried out until the biomass is liquefied to at least 50%, preferably at least 60% and most preferred at least 80%, wherein a liquefaction of from 60 to 100%, preferably from 70 to 99% is particularly preferred. The term "liquefaction" is defined by the respective measurement method as given in the method section.

The reaction temperature is preferably selected from 25 to 80° C., more preferred selected from 45 to 75° C. and particularly preferred from 48 to 70° C. In another preferred embodiment, step (a) of the process for the hydrolysis of biomass is carried out for 1 to 80 hours, preferably 2 to 40 hours, more preferred 3 to 20 hours, wherein the temperature is selected from 45 to 75° C. or from 48 to 70° C.

The enzyme composition is preferably added to the biomass in an amount of from 0.025 to 8 wt.-% of the dry matter of the biomass, more preferred 0.05 to 4 wt.-% of the dry matter of the biomass, particularly preferred being 0.08 to 2 wt.-% of the dry matter of the biomass and most preferred from 0.1 to 0.2 wt.-% of the dry matter of the biomass.

Step (a) of the process for the hydrolysis of biomass is carried out within any kind of vessel known to a person skilled in the art as suitable for the inventive process, preferably within a reactor. Suitable reactors are within the knowledge of a person skilled in the art. Preferable vessels/reactors include but are not limited to vessels/reactors comprising a stirring measure and/or a measure for pumping over or recirculating the biomass content within the reactor. Further preferred measures of preferred reactors include but are not limited to measures for temperature and/or pH-controlling and regulation of temperature and/or pH.

Following step (a) of the process for the hydrolysis of biomass as defined above, according to step (b) of the process the hydrolysis of biomass, a part of said biomass is eliminated from the vessel/reactor, within a preferred embodiment said part of biomass is continuously eliminated from the vessel/reactor. The elimination can be carried out by pumping a part of said biomass through a pipeline. Within a preferred embodiment, the volume-exchange-rate is selected from 0.05-20 $h^{-1}$. Preferred, the volume-exchange-rate is selected from 0.1-15 $h^{-1}$, more preferred from 0.5-10 $h^{-1}$. Within this context, the term "volume-exchange-rate" is to be understood as the number of times the initial reaction volume is retrieved from the vessel per hour. Selecting the exchange-rate within these ranges ensures a continuous flow of biomass within the distinct circuits. The term "reaction volume" thereby relates to total the total volume of biomass and enzyme composition present in the vessel.

The eliminated part of biomass is then subjected to a filtration according to step (c) of the process for the hydrolysis of biomass. In order to achieve maximal efficiency and throughput, steps (b) and (c) of the process for the hydrolysis of biomass are carried out in distinct circuits, preferably at least two distinct circuits. Preferred are two circuits consisting of an outer circuit and an inner circuit. The first (or preferably the outer) circuit starts with transporting and eliminating the part of biomass according to step (b) using a first pump. This biomass is then pumped into the second (or preferably the inner) circuit, which comprises a second pump and at least one filtration module. The second pump is used for transporting the eliminated part firstly to and secondly through the at least one filtration module. According to step (c) the permeate is removed from the at least one filtration module. At least a part of the filtrated biomass is withdrawn from the second (or preferably the inner) circuit after passing the at least one filtration module and fed back into the vessel according to step (d).

Both circuits/pipelines are equipped with individual hoisting-devices—such as a pump—in order to be able to select different hoisting speeds and pressures applied for both, the first and second (or preferably the outer and inner) circuit/ pipeline. Within a preferred embodiment, both circuits/ pipelines are equipped with a pump. In a particularly preferred embodiment, the hoisting device of the first circuit is placed between the vessel and the transition from the first circuit to the second circuit and the hoisting device of the second circuit is placed between the transition from the first circuit to the second circuit and the filtration module. Within a further particularly preferred embodiment, the hoisting device of the first circuit builds-up a pressure of from 0.25 to 8 bar, more preferred from 0.5 to 6 bar, most preferred from 1 to 4 bar. Within a further particularly preferred embodiment, the hoisting device of the second circuit should preferably produce a cross-flow velocity of from 0.1 to 10 m/s, more preferred of from 1 to 8 m/s, even more preferred of from 3 to 5 m/s. Further preferred is a combination of a pressure build-up of from 1 bar to 4 bar within the first circuit and a cross-flow velocity of from 3 to 5 m/s within the second circuit. The preferred ratio of the biomass-volume within the vessel to the biomass-volume within the second circuit is from 1 to 1000, more preferred from 10 to 750 and even more preferred from 20 to 500 and most preferred from 25 to 400.

In another preferred embodiment of the process for the hydrolysis of biomass the membrane is back-flushed in order to avoid clogging of the membrane. This back-flushing is achieved by increasing the pressure on the permeate side of the membrane equal or higher than the pressure on the feed side. In a preferred embodiment the pressure on the permeate side is 0 to 10 bar higher than the pressure on the feed side, more preferred 0.05 to 8 bar higher than the pressure on the feed side, even more preferred 0.1 to 6 bar higher than the pressure on the feed side, and most preferred 0.15 to 4 bar higher than the pressure on the feed side. This back-flushing can be conducted once or several times. In a preferred embodiment the membrane is back-flushed 0.05 to 120 times per hour, more preferred 0.1 to 60 times per hour, and even more preferred 0.15 to 30 times per hour, and most preferred 0.2 to 15 times per hour. In another preferred embodiment, the ratio of the sum of all back-flushing steps to the process time of step c) is 0 to 0.5, more preferred 0.001 to 0.4, even more preferred 0.002 to 0.3, and most preferred 0.004 to 0.2. The back-flushing can be carried out by using a liquid. In a preferred embodiment, this liquid is permeate, water or mixtures of permeate and water. In another preferred embodiment, further chemicals can be added to the liquid such as cleaning agents, acids, bases or any mixtures thereof. In another preferred embodiment, the cleaning effect of the back-flushing can be enhanced by injecting gas on the feed side of the permeate. In a preferred embodiment the injected gas is air.

The filtration according to step (c) of the process for the hydrolysis of biomass is preferably carried out by use of one or more filtration module(s) containing at least one filtration membrane. Preferably each filtration module is operated in a cross-flow mode. Preferably the at least one filtration membrane is an ultrafiltration membrane. Within a particularly preferred embodiment, the ultrafiltration membrane is a ceramic membrane, a stainless steel membrane, a synthetic membrane (preferably comprising polysulfone) or silicon or silicon-containing membrane or any combination thereof. Within a further particularly preferred embodiment, the cut-off of the membrane is selected from 0.5 kDa to 100 kDa, more preferred from 1 kDa to 50 kDa, even more preferred from 2 kDa to 25 kDa. Using ultrafiltration within the inventive process for the hydrolysis of biomass as described herein, a permeate product is achieved which contains a particular high amount of soluble compounds such as e.g. monomeric and dimeric sugars but is essentially free of microorganism-contaminants and larger biopolymers such as proteins and polysaccharides. Thus, the resulting permeate-product shows a long shelf-stability which could until then not be achieved without the addition of preservatives and/or by use of biological preservation. At the same time, there is not only no loss of enzymes as all the applied enzymes are retained within the biomass. Thus, the enzyme concentration even increases over time within the vessel. This constitutes a particular advantage of the inventive process for the hydrolysis of biomass as it significantly increases the reaction rate of the hydrolysis over the process time.

According to the process of the present invention for the hydrolysis of biomass, the at least one membrane of the at least one filtration module might also be a microfiltration membrane. Within a particularly preferred embodiment, the microfiltration membrane is a ceramic membrane, a stainless steel membrane, a synthetic membrane (preferably comprising polysulfone) or silicon or silicon-containing membrane or any combination thereof. This is particularly preferred for applications of the inventive process wherein the applied enzyme-composition consists predominantly of enzymes which are able to adsorb onto the solid particles of the biomass such as e.g. cellulases which possess a cellulose binding domain. An advantage of the application of a microfiltration membrane within the at least one filtration module is a relatively high permeability per time which enables the implementation of a smaller membrane-surface compared to ultrafiltration membranes.

In a particularly preferred embodiment the membrane area is 0.05 to 100 $m^2$ per 1000 kg of added biomass, further preferred 0.1 to 70 $m^2$ per 1000 kg of added biomass, more preferred 0.2 to 50 $m^2$ per 1000 kg of added biomass and most preferred 0.4 to 25 $m^2$ per 1000 kg of added biomass.

The permeate-product obtained by the filtration is preferably continuously removed and may also be collected within a second vessel. In addition, according to step (d) of the process for the hydrolysis of biomass, the remaining filtrated or preferably part of the remaining filtrated biomass is fed back to the vessel. In case only a part of the filtrated biomass is fed back to the vessel, the rest of biomass is pumped within the second (or preferably the inner circuit). The preferred ratio of the flow that is fed back into the hydrolysis vessel (step d) to the permeate flow (step c) is from 0.05 to 50, more preferred from 0.1 and 25, and even more preferred from 0.25 and 10 and most preferred from 0.5 and 5. The ratio of biomass fed back to the vessel to the part of the biomass pumped within the second (or preferably the inner) circuit is determined by the flow rate of biomass from the vessel into the outer circuit and the permeate flow through the at least one filtration module.

It is a particular advantage of the inventive process for the hydrolysis of biomass if—according to a further optional step (e)—an amount of liquid is added to the biomass corresponding to the amount of liquid removed after filtration within the permeate-product according to step c) of the process. The term "liquid added corresponding to the amount of liquid within the permeate-product" is to be understood in that the liquid added amounts to at least 10 vol.-%, preferably at least 25 vol.-%, more preferably at least 50 vol.-%, more preferred at least 70 vol.-% of the liquid within the permeate product and is further preferred selected from 50 to 150 vol.-%, preferably 70 to 130 vol.-% and most preferred from 80 to 120 vol.-% of the liquid within the permeate product which is removed each time during step c) of the process. It is particularly preferred if the volume of liquid added equals the volume of the permeate product. In another preferred embodiment, the liquid is added continuously. Thus, the amount of liquid added to the biomass during optional step e) compensates at least partially for the volume removed according to step c).

Within a particularly preferred embodiment of the process for the hydrolysis of biomass, the amount of liquid corresponding to the amount removed by filtration is added directly into the vessel. In another particularly preferred embodiment of the process for the hydrolysis of biomass, the amount of liquid corresponding to the amount removed by filtration is added by back-flushing the membrane as described above.

It is, however, also within the scope of the present invention to add the liquid at any other stage of the process for the hydrolysis of biomass known to a person skilled in the art as suitable for the inventive purpose. Preferably, the amount of liquid is added to the filtrated biomass, i.e. after carrying out step (c) of the process for the hydrolysis of biomass. More preferably, the amount of liquid is added to the filtrated biomass after the content of the vessel has been reduced to from 0.25 to 40% of the initial non-filtrated volume, most preferably once it has been reduced to from 0.5 to 30% of the initial non-filtrated volume, even more preferably once it has been reduced to from 1 to 20%. The addition of an amount of liquid corresponding to the amount removed during filtration is particularly advantageous as an increase in yield is achieved by flushing the small percentage of insoluble rests of biomass remaining in the system after the hydrolysis and carrying with it the rests of soluble sugar still present on the surface of the solids through the membrane. Preferably the liquid added is water.

In embodiments of the inventive process for the hydrolysis of biomass without the addition of liquid according to step (e) of the process, the filtrated biomass still contains the same concentration of saccharides as the permeate. This embodiment of the inventive process might be advantageous for applications of the filtrated biomass (equals in this case the protein-containing product) as a fermentation substrate or supplement to a fermentation medium.

It is also preferred within the present invention to add fresh biomass during the process the hydrolysis of biomass according to step (f) Addition of fresh biomass.

This addition can be done at any time of the process. In a preferred embodiment, the percentage of the biomass present in the vessel at the start of the process compared to the sum of all biomass processed is at least 1 wt.-%, preferably at least 5 wt.-%, more preferred at least 10 wt.-% and most preferred at least 15 wt.-%. It is particularly preferred to select the percentage of the biomass present in the vessel at the start of the process compared to the sum of all biomass processed from the range of from 1 to 40 wt.-%, preferably from 5 to 35 wt.-% and particularly preferred of from 10 to 25 wt.-%. This embodiment is preferred as the addition of parts of the total biomass at different times of the process is advantageous as there is no need to store major amounts of fresh biomass before subjecting it to the inventive process.

In another preferred embodiment, the addition of fresh biomass stops at least 1 hour before the process is stopped, preferably at least 2 hours before the process is stopped, more preferred at least 3 hours before the process is stopped and most preferred at least 4 hours before the process is stopped. Especially preferred is that the addition of flesh biomass stops at least 1 hour before step (e) is started, preferably at least 2 hours before step (e) is started, more preferred at least 3 hours before step (e) is started and most preferred at least 4 hours before step (e) is started.

Within a preferred embodiment of the process for the hydrolysis of biomass, steps (b) to (e) or steps (b) to (f) are repeated at least once to ensure the at most possible yield of the desirable compounds of the biomass. Within a particularly preferred embodiment, steps (b) to (e) or steps (b) to (f) are repeated from 2 to 10000 times, preferably from 10 to 7000 times, more preferred from 50 to 5000 times and most preferred from 100 to 1000 times. Within a further preferred embodiment of the process for the hydrolysis of biomass, steps (b) to (e) or steps (b) to (f) are repeated until the content of remaining soluble hexoses in the filtrated biomass is less than 4 wt.-% with respect to the initial total hexoses content in the biomass, preferably less than 2 wt.-%, even more preferred less than 1 wt.-% and most preferred less than 0.5 wt.-%. Within a particularly preferred embodiment of the process for the hydrolysis of biomass, steps (b) to (e) or steps (b) to (f) are carried out in a way to enable a continuous process.

Within the process for the hydrolysis of biomass according to the present invention, it is particularly advantageous if steps (a) and (b) are carried out concurrently for at least 80% of the time period of step (a), preferably from 50 to 95%, particularly preferred from 60 to 90% and most preferred from 70 to 85%.

Within the process for the hydrolysis of biomass according to the present invention, it is particularly advantageous if steps (a) and (c) are carried out concurrently for at least 80% of the time period of step (a), preferably from 50 to 95%, particularly preferred from 60 to 90% and most preferred from 70 to 85%.

Within the process for the hydrolysis of biomass according to the present invention, it is particularly advantageous if steps (a) and (d) are carried out concurrently for at least 80% of the time period of step (a), preferably from 50 to 95%, particularly preferred from 60 to 90% and most preferred from 70 to 85%.

Within the process for the hydrolysis of biomass according to the present invention, it is particularly advantageous if steps (a) and (e) are carried out concurrently for at least 0.1% of the time period of step (a), preferably from 1 to 40%, particularly preferred from 2 to 30% and most preferred from 3 to 20%.

In a particularly preferred embodiment of the process for the hydrolysis of biomass, the enzyme composition added to the biomass is in an amount of from 0.05 to 0.15 wt.-% of dry matter of the biomass and the process step b) is started after 3 to 7 hours. In another particularly preferred embodiment of the process the enzyme composition added to the biomass is in an amount of from 0.15 to 0.25 wt.-% of dry matter of the biomass and the process step b) is started after 2 to 6 hours. The process of the present invention for the hydrolysis of biomass enables to obtain a permeate-product with a high content of saccharides in terms of monomeric and oligomeric sugars which shows a particularly long shelf stability as it is completely free of microbial contaminants. For this reason, the permeate-product obtainable by the process according to the present invention is also highly suitable for food and feed applications. Further, the permeate-product is highly suitable for pharmaceutical applications.

The present invention therefore comprises in another aspect a saccharide-containing permeate-product, produced by a process as defined within the present invention.

Within a preferred embodiment of the present invention, the permeate product comprises at least 80 g per liter saccharides, preferably 100 g per liter, more preferred 120 g per liter and most preferred 130 g per liter. Within a preferred embodiment of the present invention, the permeate product comprises at least 50 g per liter fructose, preferably at least 60 g per liter fructose and also preferred is a fructose content of from 50 to 100 g per liter. Within a further preferred embodiment of the present invention, the permeate product comprises at least 50 g per liter glucose, preferably at least 60 g per liter glucose and also preferred is a glucose content of from 50 to 100 g per liter, wherein it is particularly preferred that the general amount of monomeric and dimeric sugars is from 80 g per liter to 200 g per liter.

The process of the present invention for the hydrolysis of biomass further enables to obtain a protein-containing product with a high content of proteins and low sugar content, preferably a sugar content below 4 wt.-% but a high content of nitrogen which is preferably in the range from 0.2 to 5 wt.-%, further preferred in the range from 0.3 to 4 wt.-%. The protein-containing product obtainable by the process of the present invention is therefore highly suitable as a supplement to commercial fermentation media or as a fermentation medium basis or for food and feed applications.

The present invention therefore comprises in another aspect a protein-containing product, produced by a process as defined within the present invention.

Within a preferred embodiment of the present invention, the protein-containing product comprises at least 1 wt.-% protein, preferably at least 2.5 wt.-% protein, more preferred at least 5 wt.-% protein, even more preferred at least 7.5 wt.-% protein and most preferred at least 10 wt.-% protein.

In a further aspect, the present invention is directed to the use of the protein-containing product for the production of a fermentation medium or for food and feed applications in which high protein contents are beneficial. As the protein-containing product further contains a considerable high amount of nitrogen, the protein-containing product is particularly suitable as a supplement to fermentation media for the production of enzymes.

In another aspect the present invention relates to a process for the production of organic compounds from the saccharide-containing permeate-product as defined above, comprising the steps:
a) Contacting the saccharide-containing permeate-product with at least one microorganism selected from yeast, bacteria, fungi and mixtures thereof capable of converting the permeate product to at least one organic compound;
b) Fermentation of the saccharide-containing permeate-product;
c) Separating the organic compound.

According to the process for the production of organic compounds, the temperature during contacting the saccharide-containing permeate-product with the at least one microorganism is selected from 10 to 65° C., preferably from 15 to 55° C., especially preferred from 20 to 50° C., most preferred from 25 to 45° C.

It is particularly preferred to use mesophilic yeasts such as all apecies of genus *Saccaromyces*, especially *Saccharomyces bayanus, Saccharomyces boulardii, Saccharomyces bulderi, Saccharomyces cariocanus, Saccharomyces cariocus, Saccharomyces cerevisiae, Saccharomyces chevalieri, Saccharomyces dairenensis, Saccharomyces ellipsoideus, Saccharomyces eubayanus, Saccharomyces exiguus, Saccharomyces florentinus, Saccharomyces kluyveri, Saccharomyces martiniae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvaruin, Saccharomyces zonatus*, as well as *Arxula adeninovorans, Ashbya gossypii, Hansenula polymoipha, Debaramyces hansenii, Hortea werneckii, Kluyeveromyces lactis, Schwanniomyces occidentalis, Thrichosporon domesticum, Thrichosporon montevideense, Xanthophyllornyces dendrohous, Yarowia lypolytica, Zygosaccharomyces bailii, Zygosaccharornyces rouxii, Schizosaccharomyces pombe, Pichia stipitis, Pichia segobiensis, Candida shehatae, Candida tropicalis, Candida boidinii, Candida tenuis, Pachysolen tannophilus, Hansenula polymorpha, Candida famata, Candida parapsilosis, Candida rugosa, Candida sonorensis, Candida maltose, Issatchenkia terricola, Kloeckera apis, Pichia barkeri, Pichia cactophila, Pichia deserticola, Pichia norvegensis, Pichia membranefaciens, Pichia mexicana* and *Torulaspora delbrueckii* and mixtures thereof.

In an alternative embodiment of the process for the production of organic compounds from the saccharide-containing permeate-product, thermophilic micro-organisms are used. Examples of thermophilic yeasts suitable for the inventive process are *Candida bovina, Candida picachoensis, Candida emberorum, Candida pintolopesii, Candida thermophile, Kluyveromyces marxianus, Kluyveromyces fragilis, Kazachstania telluris, Issatchenkia orientalis* and *Lachancea thermotolerans*. Preferred thermophylic bacteria include *Clostridium thermocellum, Clostridium thermohydrosulphuricum, Clostridium thermosaccharolyticton, Thernwanaerobizon brockii, Thermobacteroides acetoethylicus, Thermoanaerobacter ethanolicus, Clostridium thermoaceticum, Clostridium thernwautotrophicum, Acetogeniwn kivui, Desulfotomaculum nigrificans and Desulvovibrio thermophilus, Thermoanaerobacter tengcongensis, Bacillus stearothermophilus* and *Thermoanaerobacter mathranii*.

The use of the following mesophilic yeasts is especially preferred: *Saccharomyces cerevisiae, Pichia stipitis, Pachysolen tannophilus, Candida shehatae*.

In an alternative embodiment of the process for the production of organic compounds from the saccharide-containing permeate-product fungi are used. Examples of fungi suitable for the inventive process are *Aspergillus* sp., *Trichoderma* sp., *Penicillium* sp., *Acremonium* sp., *Rhizopus* sp. and *Talaromyces* sp.

In an alternative embodiment of the process for the production of organic compounds from the saccharide-containing permeate-product bacteria are used. Examples of bacteria suitable for the inventive process are *Clostridium acetobutylicum, Lactobacillus brevis, Lactobacillus bulgaricus, Lactobacillus casei, Lactobacillus helveticus, Lactobacillus lactis, Lactococcus lactis, Leuconostoc mesenteroides, Lactobacillus* sp., *Zymomonas mobilis, Escherichoia coli*.

Fermentation is preferably conducted in a batch mode (discontinuous), in the fed-batch mode or in a continuous mode. Most preferably, fermentation is conducted in the batch mode.

Within a preferred embodiment, minerals such as copper, zinc, magnesium, calcium, iron and nitrogen-containing compounds such as nitrate, amino acids, ammonia are added to the saccharide-containing permeate-product prior to step a) of the process for the production of organic compounds. Within a particularly preferred embodiment of the process for the production of organic compounds, a part of the protein-containing product is added to the fermentation medium.

Valuable organic compounds resulting from bacterial fermentation of the saccharide-containing permeate-product comprise but are not limited to organic acids (such as acetic acid, lactic acid, succinic acid, itaconic acid, fumaric acid, propionic acid, and glucuronic acid), amino acids (such as glutamic acid, leucine, lysine, threonine, aspartic acid, phenylalanine, cysteine), caprolactams (such as alpha-aminocaprolactam), antibiotics (such as bleomycin, virginiamycin, lincomycin, monensin, blasticidin, tetracycline), vitamins (such as vitamin B2, B12 and C), enzymes, nucleotides/nucleosides (such as NADH, ATP, cAMP, FAD, coenzyme A), biogas, biopolymers (such as polyhydroxybutyrate, polyamides/fibroins), proteins, polysaccharides (such as xanthan, dextran), amino glucans (such as hyaluronic acid) as well as organic solvents and biofuels (such as acetone, ethanol, butanol, propanediol).

Valuable organic compounds resulting from yeast fermentation of the saccharide-containing permeate-product comprise but are not limited to organic solvents (e.g. ethanol, propanol), nucleotides (e.g. RNA), biosurfactants (e.g. sophorose lipids), enzymes, and biopolymers (e.g. spidroins).

Valuable organic compounds resulting from fungal fermentation of the saccharide-containing permeate-product comprise organic acids (such as citric acid, fumaric acid, itaconic acid), antibiotics (such as penicillin, cephalosporin), enzymes, and polysaccharides (such as chitin).

In a further preferred embodiment of this process the organic compound is selected from alcohols, organic acids, biopolymers, antibiotics, amino acids, caprolactams, polysaccharides, organic solvents, biofuels, aminoglucans, nucleotides/nucleosides, vitamins, biosurfactants, enzymes and mixtures thereof.

It was further surprisingly found that the protein-containing product obtained by the inventive process was an excellent fermentation substrate or supplement of commercial fermentation media for bacterial, yeast and fungal organisms producing value adding products such as enzymes, pharmaceuticals or chemical products. The protein-containing product could thereby also serve as the basis for the production of a fermentation medium.

Within a further aspect the present invention therefore pertains to the use of the protein-containing product as defined above for the production of a fermentation medium.

Preferred fermentation processes include the fermentation of the saccharides to ethanol using *Saccharomyces cerevisiae* or to lactic acid using a *Lactobacillus* strain or to itaconic acid using *Aspergillus terreus*. Especially preferred is that these fermentations are carried out without any supplements.

In the following particularly preferred embodiments of the present invention are described which are not to be understood as limiting the invention in any respect.

Particularly Preferred Embodiment 1

Particularly preferred is a process for the hydrolysis of biomass comprising the steps of
a) Contacting the biomass with an enzyme-composition containing at least one enzyme selected from the class of hydrolases in a vessel;
b) Eliminating a part of said biomass;
c) Subjecting said part of biomass to a filtration and removing the permeate;
d) Backfeeding of at least part of the filtrated biomass to the vessel;
e) Addition of an amount of liquid corresponding to the amount removed by filtration according to step c);
wherein step b) and step e) of the process are carried out in distinct circuits and
wherein the filtration is carried out by use of at least one filtration module comprising at least one ultrafiltration membrane. Within this preferred embodiment, it is further preferred that the enzyme-composition contains cellulases, hemicellulases and/or pectinases.

Particularly Preferred Embodiment 2

Particularly preferred is a process for the hydrolysis of biomass comprising the steps o
a) Contacting the biomass with an enzyme-composition containing at least one enzyme selected from the class of hydrolases in a vessel;
b) Eliminating a part of said biomass;
c) Subjecting said part of biomass to a filtration and removing the permeate;
d) Backfeeding of at least part of the filtrated biomass to the vessel;
e) Addition of an amount of liquid corresponding to the amount removed by filtration according to step c);
wherein step b) and step c) of the process are carried out in at least two distinct circuits i.e. at least one inner and an outer circuit wherein each circuit is equipped with a hoisting device such as a pump and the inner circuit further comprises at least one filtration module which comprises preferably at least one ultrafiltration membrane;
wherein the pressure applied by the pump of the outer circuit is preferably selected from 0.25 to 8 bar, more preferred from 1 to 4 bar and wherein the cross-flow velocity of the at least one inner circuit each is selected from 0.1 to 10 m/s, preferably 3 to 5 m/s.

Particularly Preferred Embodiment 3

Particularly preferred is a saccharide-containing permeate-product, produced by a process as defined within the present invention with a saccharide content of at least 100 g per liter saccharides wherein it is most preferred that at least 40 wt-% of this saccharide content is glucose.

Particularly Preferred Embodiment 4

Particularly preferred is a protein-containing product, produced by a process as defined within the present invention with a sugar content below 4 wt.-% but a high content of nitrogen, wherein a nitrogen content of from 0.3 to 4 wt.-%. is preferred.

Methods

Determining the Percentage of Liquefaction of Biomass

The reaction mixture (20 mL) of the enzyme-composition and biomass with a d.m. content of 15% is mixed with 50 mM sodium acetate buffer (pH 5). The mixture is incubated for 30 min to 5 hours at 50° C. Afterwards, the reaction mixture is centrifuged for 30 min at 3200 g and the liquid supernatant is separated and weighed. 1 ml of the supernatant is heat inactivated at 95° C. for 10 min and the amount of sugar released is analyzed by HPLC (Agilent®, Germany) with an Aminex HPX 87® (SioRad Labs, Hercules, USA) ion exchange column (Eluent: 100% water, T: 85° C., Flow: 0.6 ml/min, RI detection).

The liquefaction is determined according the formula:

$$\frac{\text{net weight of supernatant}}{20} \times 100.$$

EXAMPLES AND FIGURES

The present invention is now described by the following examples and figures. All examples and figures are for illustrative purposes only and are not to be understood as limiting the invention.

FIG. 1 shows how by the particular combination of steps a) to e) of the inventive process for the hydrolysis of biomass the enzyme concentration increases over time within the vessel with ongoing filtration according to step c) of the process. Further, the reaction rate of the hydrolysis increases with ongoing filtration according to step c) and addition of liquid according to step e) of the process.

FIG. 5 shows an exemplary process setup suitable for carrying out the process for the hydrolysis of biomass according to the invention implementing one outer and two inner circuits in parallel.

Figure 1:
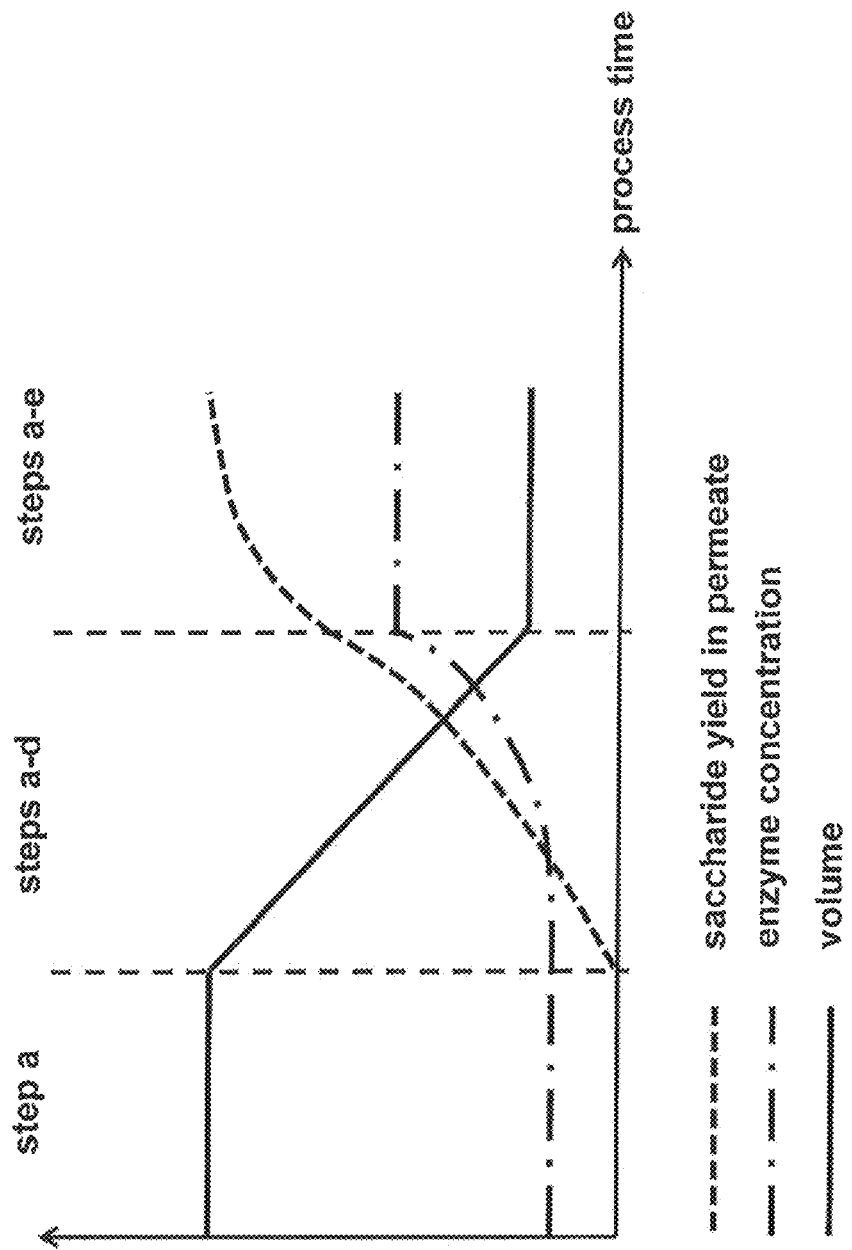

FIG. 1 Illustration of Temporal Courses for Volume, Enzyme Concentration and Saccharide Yield During the Process of the Invention The process is started by contacting the biomass with the enzyme-composition (step a). Within the period in which only step (a) is carried out, the volume and the enzyme concentration remain constant and a part of the biomass is hydrolyzed.

After a certain time period, steps (b), (c) and (d) are started additionally to step (a). Due to the removal of permeate the volume decreases and saccharides are obtained within the permeate. Therefore, the saccharide yield increases. Since the enzymes are retained by the membrane, the enzyme concentration increases, which improves the hydrolysis.

When the volume reaches are certain minimum value, step (e) is additionally started by continuously adding the same amount of water as permeate is removed, Therefore, the volume remains constant as well as the enzyme concentration. The saccharides are washed out and so the saccharide yield increases further.

When the economic optimum between addition of water and increase of saccharide yield is reached, the process is stopped.

Figure 2:
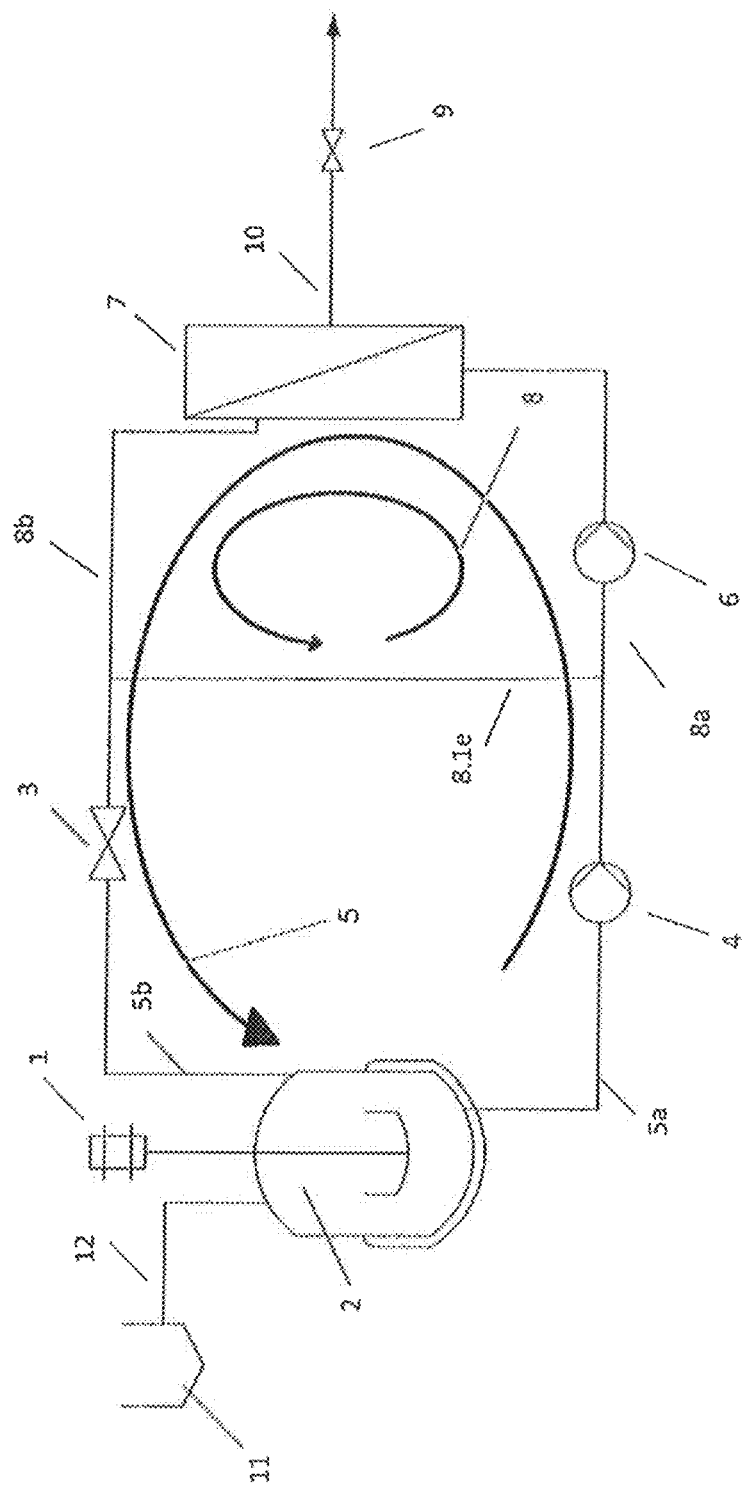
FIG. 2 shows an exemplary process setup suitable for carrying out the process for the hydrolysis of biomass according to the invention implementing one filtration module and two circuits (inner and outer circuit).

FIG. 2 Exemplary Process Setup Implementing One Filtration Module and Two Circuits (Inner and Outer Circuit)

Carrying out the process for the hydrolysis of biomass according to the present invention by use of a process set-up according to FIG. 2, biomass is fed into the vessel (2) which is equipped with a stirrer (1). After (at least) partially carrying out step a) according to the process within the vessel (2), a part of biomass is eliminated according to step b) of the process and conveyed to the outer circuit (5) by use of a first pipeline (5a) and pumped by a first pump (4) to the inner circuit (8).

Within the inner circuit (8) the eliminated part of biomass is conveyed to a second pump (6) by use of a second pipeline (8a). The second pump (6) is operated separately from the first pump (4) thereby selecting a pump-rate in order to achieve the required cross-flow velocity. The second pump (6) is pumping the eliminated part of biomass to the filtration module (7) in order to subject the biomass to a filtration according to step c) of the process. The permeate is then removed from the filtration module (7) through a pipeline (10) wherein the output volume is controlled by a valve (9).

The filtrated biomass is then further transported within the inner circuit (8) by a third pipeline (8b) to the outer circuit (5) wherein the at least part of the volume of the filtrated biomass which is fed back to the vessel according to step d) of the process through a fourth pipeline (5b) is regulated by a valve (3). In case only a part of the filtrated biomass is fed back to the vessel (2) the rest of the filtrated biomass is circulated within the inner circuit (8) by use of a pipeline (8.1e). An amount of liquid corresponding to the amount removed during filtration is added to the vessel (2) from a reservoir (11) through a pipeline (12).

Figure 3:
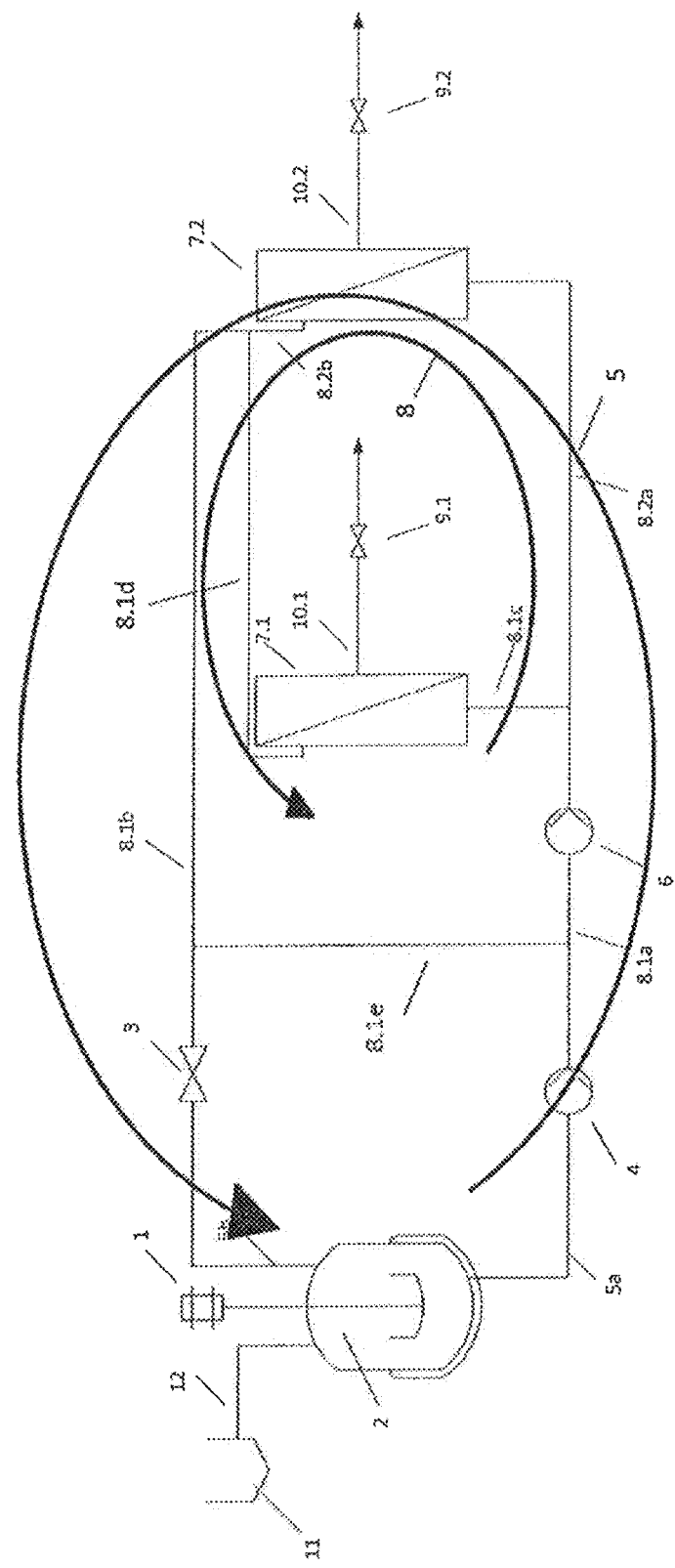
FIG. 3 shows an exemplary process setup suitable for carrying out the process for the hydrolysis of biomass according to the invention implementing two circuits (inner and outer circuit) and two filtration modules in parallel within the inner circuit.

FIG. 3 Exemplary Process Setup Implementing Two Circuits (Inner and Outer Circuit) and Two Filtration Modules in Parallel within the Inner Circuit Carrying out the process for the hydrolysis of biomass according to the present invention by use of a process set-up according to FIG. 3 biomass is fed into the vessel (2) which is equipped with a stirrer (1). After (at least) partially carrying out step a) according to the process within the vessel (2), a part of biomass is eliminated according to step b) of the process and conveyed to the outer circuit (5) by use of a first pipeline (5a) and pumped by a first pump (4) to the inner circuit (8).

Within the inner circuit (8) the eliminated part of biomass is conveyed to a second pump (6) by use of a second pipeline (8.1a). The second pump (6) is operated separately from the first pump (4) thereby selecting a pump-rate in order to achieve the required cross-flow velocity. The second pump (6) is pumping the eliminated part of biomass to the first filtration module (7.1) by use of a pipeline (8.1c) in order to subject the biomass to a filtration according to step c) of the process but also, concurrently, by use of a pipeline (8.2a) to the second filtration module (7.2). Thus, according to the exemplary process setup according to FIG. 3 the first and second filtration module (7.1) and (7.2) can be operated parallel. The permeate is then removed from the first filtration module (7.1) and the second filtration module (7.2) through a pipeline (10.1) and a pipeline (10.2) wherein the output volume is controlled independently by a valve (9.1) and a valve (9.2).

The filtrated biomass is then further transported within the inner circuit (8) by a pipeline (8.1b), (8.1d) and by a pipeline (8.2b) to the outer circuit (5) wherein the volume of the filtrated biomass which is fed back to the reactor according to step d) of the process through a pipeline (5b) is regulated by a valve (3).). In case only a part of the filtrated biomass is fed back to the vessel (2) the rest of the filtrated biomass is circulated within the inner circuit (8) by use of a pipeline (8.1e). An amount of liquid corresponding to the amount removed during filtration is added to the vessel from a reservoir (11) through a pipeline (12).

Figure 4:
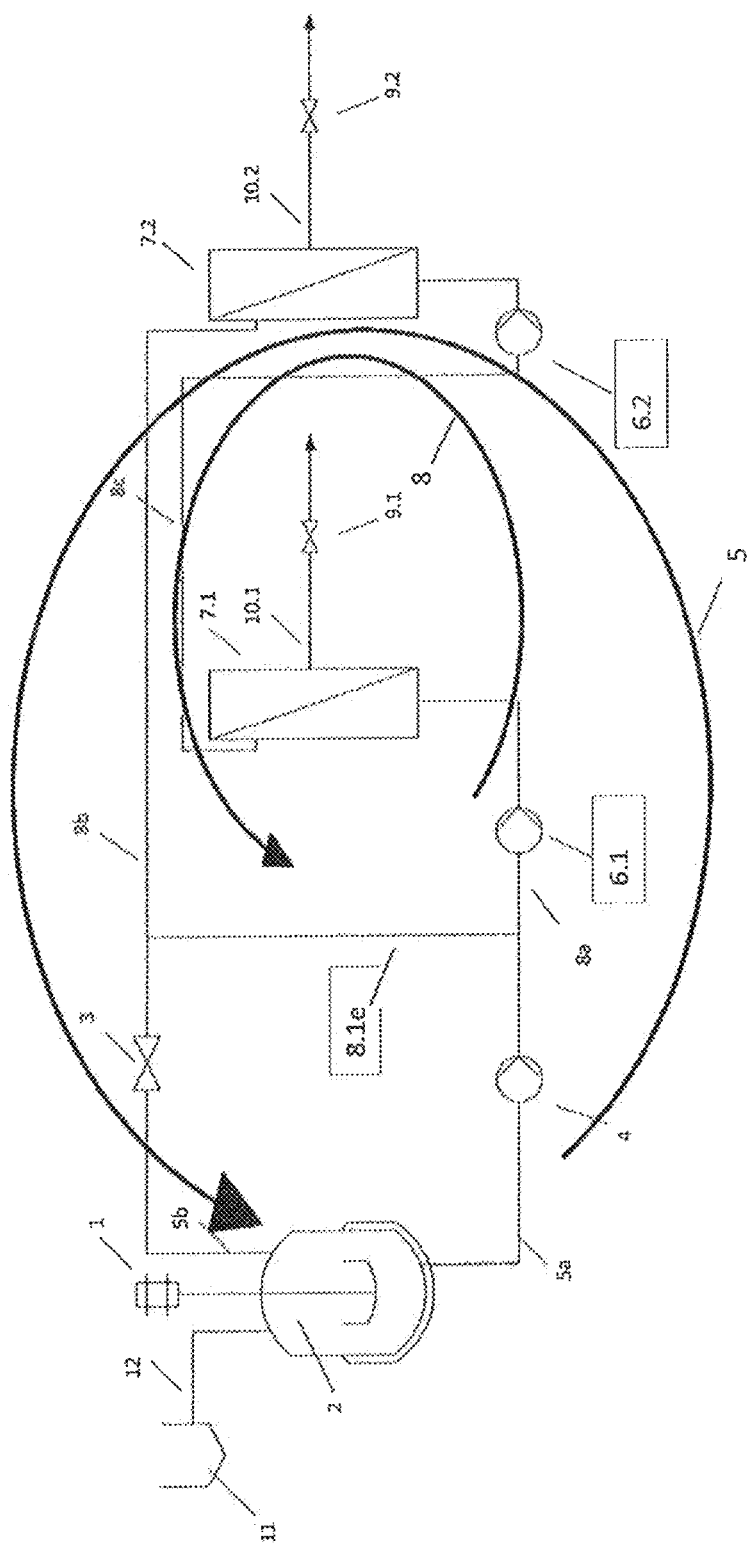
FIG. 4 shows an exemplary process setup suitable for carrying out the process for the hydrolysis of biomass according to the invention implementing two circuits (inner and outer circuit) and two filtration modules in series within the inner circuit.

FIG. 4 Exemplary Process Setup Implementing Two Circuits (Inner and Outer Circuit) and Two Filtration Modules in Series within the Inner Circuit Carrying out the process for the hydrolysis of biomass according to the present invention by use of a process set-up according to FIG. 4 biomass is fed into the vessel (2) which is equipped with a stirrer (1). After (at least) partially carrying out step a) according to the process within the vessel (2), a part of biomass is eliminated according to step b) of the process and conveyed to the outer circuit (5) by use of a first pipeline (5a) and pumped by a first pump (4) to the inner circuit (8).

Within the inner circuit (8) the eliminated part of biomass is conveyed to a second pump (6.1) by use of a second pipeline (8a). The second pump (6.1) is operated separately from the first pump (4) thereby selecting a pump-rate in order to achieve the required cross-flow velocity. The second pump (6.1) is pumping the eliminated part of biomass to the first filtration module (7.1) in order to subject the biomass to a filtration according to step c) of the process. The permeate is then removed from the first filtration module (7.1)) through a pipeline (10.1) wherein the output volume is controlled independently by a valve (9.1).

The filtrated biomass is then further transported within the inner circuit (8) by a pipeline (8c) and pumped by a third pump (6.2) to the second filtration module (7.2) thereby selecting a pump-rate in order to achieve the required cross-flow velocity. The third pump (6.2) is also operated separately from the first pump (4) and the second pump (6.1). The permeate is then removed from the second filtration module (7.2) through a pipeline (10.2) wherein the output volume is controlled independently by a valve (9.2). Thus, according to the exemplary process setup according to FIG. 4 the first and second filtration module (7.1) and (7.2) can be operated in series.

The filtrated biomass is then further transported within the inner circuit (8) by a pipeline (8b) to the outer circuit (5) wherein the volume of the filtrated biomass which is fed back to the reactor according to step d) of the process through a pipeline (5b) is regulated by a valve (3). In case only a part of the filtrated biomass is fed back to the vessel (2) the rest of the filtrated biomass is circulated within the inner circuit (8) by use of a pipeline (8.1e). An amount of liquid corresponding to the amount removed during filtration is added to the vessel from a reservoir (11) through a pipeline (12).

FIG. 5 Exemplary Process Setup Implementing One Outer and Two Inner Circuits in Parallel Carrying out the process for the hydrolysis of biomass according to the present invention by use of a process set-up according to FIG. 5 biomass is fed into the vessel (2) which is equipped with a stirrer (1). After (at least) partially carrying out step a) according to the process within the vessel (2), a part of biomass is eliminated according to step b) of the process and conveyed to the outer circuit (5) by use of a first pipeline (5a) and pumped by a first pump (4) to the first inner circuit (8.1) and concurrently to the second inner circuit (8.2).

Within the first inner circuit (8.1) the eliminated part of biomass is conveyed to a second pump (6.1) by use of a pipeline (8.1a). The second pump (6.1) is operated separately from the first pump (4) thereby selecting a pump-rate in order to achieve the required cross-flow velocity. The second pump (6.1) is pumping the eliminated part of biomass to the first filtration module (7.1) in order to subject the biomass to a filtration according to step c) of the process.

Within the second inner circuit (8.2) the eliminated part of biomass is conveyed to a third pump (6.2) by use of a pipeline (8.2a). The third pump (6.2) is operated separately from the first pump (4) and the second pump (6.1) thereby selecting a pump-rate in order to achieve the required cross-flow velocity. The third pump (6.2) is pumping the eliminated part of biomass to the second filtration module (7.2) in order to subject the biomass to a filtration according to step c) of the process. Thus, according to the exemplary process setup according to FIG. 5 the first and second inner circuit (8.1) and (8.2) can be operated parallel.

The permeate is then removed from the first filtration module (7.1) and the second filtration module (7.2) through a pipeline (10.1) and a pipeline (10.2) wherein the output volume is controlled independently by a valve (9.1) and a valve (9.2). The filtrated biomass is then further transported within the first inner circuit (8.1) by a pipeline (8.1b) and within the second inner circuit (8.2) by a pipeline (8.2b) to the outer circuit (5) wherein the volume of the filtrated biomass which is fed back to the reactor according to step d) of the process through a pipeline (5b) is regulated by a valve (3). In case only a part of the filtrated biomass is fed back to the vessel (2) the rest of the filtrated biomass is circulated within the inner circuit (8.1) and/or the inner circuit (8.2) by use of a pipeline (8.1e). An amount of liquid corresponding to the amount removed during filtration is added to the vessel from a reservoir (11) through a pipeline (12).

EXAMPLE 1

Whole sugar beet material was prepared from fresh sugar beet roots sampled in Bedburg, Germany. Beet roots were washed to remove remaining soil and cut. The material was then treated by a high shear mixer in order to allow pumping. The sugar beet material on average had a d.m. content of 22%.

The following enzymes were used: 43.4%(w/w) Celluclast®, 6.3%(w/w) Novo 188® and 50.3% (w/w) Pectinex Ultra SP-L®. These products were mixed in 50 mM NaAc buffer (pH 5).

This enzyme mixture was mixed with 200 kg fresh sugar beet material at 0.2% wt.-% E/S. The final reaction mixture contained 18% d.m. of sugar beet material. The mixture was incubated with slight stirring at 50° C. After incubation for 4 hours, the ultrafiltration step was started using two circuits equipped each with a pump (one for increasing the trans-membrane pressure and one for the transportation of the biomass through the membrane unit). The membrane used was a ceramic membrane with 10 kDa cut-off (GEA Filtration, GEA Wiegand GmbH). The transmembrane pressure applied was 0.5-3 bar and the cross-flow velocity was 3-4 m/s. The resulting permeate flux was 15-20 L/h. After 9 h of ultrafiltration, deionized water was added into the reactor at 15-20 L/h, while the filtration was continued at the same permeate flow rate. After 2 h the process was stopped. The final permeate mass and retentate mass recovered were 180 kg and 16 kg, respectively. The C6 sugar yield was >98% and the liquefaction reached >85 wt.-%.

Samples were subsequently applied to HPLC analysis. The resulting hydrolysis mixture was analyzed by HPLC (Agilent, Germany) with an Aminex HPX 87 (BioRad Labs, Hercules, USA) ion exchange column (Eluent: 100% water, T: 85° C., Flow: 0.6 ml/min, RI detection).

The results are shown in table 1.

|  | Permeate obtained during step b) to d) | Permeate obtained during step b) to e) | Filtrated biomass (final composition) |
| --- | --- | --- | --- |
| Glucose [g/l] | 74 | 34 | 12 |
| Fructose [g/l] | 77 | 36 | 11 |
| Arabinose [g/l] | 7 | 4 | 1 |
| Cellobiose [g/l] | 6 | 4 | 1 |

Table 1 shows the obtained sugar concentrations in permeate obtained during step b) to d), permeate obtained during step b) to e) and filtrated biomass (the error is estimated to +/−10%)

EXAMPLE 2

Whole sugar beet material was prepared from fresh sugar beet roots sampled in Bedburg, Germany. Beet roots were washed to remove remaining soil and. The material was then treated by a high shear mixer in order to allow pumping. The sugar beet material on average had a d.m. content of 22%.

The following enzymes were used: 43.4% (w/w) Celluclast®, 6.3%(w/w) Novo 188® and 50.3% (w/w) Pectinex Ultra SP-L®. These products were mixed in 50 mM NaAc buffer (pH 5).

This enzyme mixture was mixed with 150 kg fresh sugar beet material at 0.1% wt.-% EIS. The final reaction mixture contained 18% dm. of sugar beet material. The mixture was incubated with slight stirring at 50° C. After incubation for 5 hours, the ultrafiltration step was started using two circuits equipped each with a pump (one for increasing the transmembrane pressure and one for the transportation of the biomass through the membrane unit). The membrane used was a ceramic membrane with 10 kDa cut-off (GEA Filtration, GEA Wiegand GmbH). The transmembrane pressure applied was 0.5-3 bar and the cross-flow velocity was 3-4 m/s. The resulting permeate flux was 10-20 L/h. After 9 h of ultrafiltration, deionized water was added into the reactor at 10-20 L/h, while the filtration was continued at the same permeate flow rate. After 1.5 h the process was stopped. The final permeate mass and retentate mass recovered were 126 kg and 16 kg, respectively. The C6 sugar yield was >90% and the liquefaction reached >80 wt.-%.

Samples were subsequently applied to HPLC analysis. The resulting hydrolysis mixture was analyzed by HPLC (Agilent, Germany) with an Aminex HPX 87 (BioRad Labs, Hercules, USA) ion exchange column (Eluent: 100% water, T: 85° C., Flow: 0.6 ml/min, RI detection).

The results are shown in table 2.

|  | Permeate obtained during step b) to d) | Permeate obtained during step b) to e) | Filtrated biomass (final composition) |
| --- | --- | --- | --- |
| Glucose [g/l] | 75 | 45 | 23 |
| Fructose [g/l] | 72 | 44 | 22 |
| Arabinose [g/l] | 7 | 5 | 2 |
| Cellobiose [g/l] | 7 | 6 | 3 |

Table 2 shows the obtained sugar concentrations in permeate obtained during step h) to d), permeate obtained during step b) to e) and filtrated biomass (the error is estimated to +1-10%)

COMPARATIVE EXAMPLE 2

Whole sugar beet material was prepared according to example 2.

The following enzymes were used: 43.4%(w/w) Celluclast®, 6.3%(w/w) Novo 188® and 50.3% (w/w) Pectinex Ultra These products were mixed in 50 mM NaAc buffer (pH 5).

This enzyme mixture was mixed with 150 kg fresh sugar beet material at 0.1 wt.-% E/S. The final reaction mixture contained 18% dm. of sugar beet material in 50 mM sodium acetate buffer (pH5).

The reaction mixture was incubated for 30 min to 5 hours at 50° C. After liquefaction and hydrolysis the reaction mixture was centrifuged for 30 min at 3200 g and the liquid supernatant was separated and weighted. 1 ml of the supernatant was heat inactivated at 95° C. for 10 min and the amount of sugar released was analyzed by HPLC (Agilent, Germany) with an Aminex HPX 87 (BioRad Labs, Hercules, USA) ion exchange column (Eluent: 100% water, T: 85° C., Flow: 0.6 ml/min, RI detection).

The results are shown in table 3

|  | Supernatant |
| --- | --- |
| Glucose [g/l] | 54 |
| Fructose [g/l] | 53 |
| Arabinose [g/l] | 9 |
| Cellobiose [g/l] | 5 |

Table 3 shows the obtained sugar concentrations in the supernatant.

Since the supernatant of comparative example 2 has a lower sugar concentration compared to the permeate of example 2 the process according to the invention was more efficient.

EXAMPLE 3

Ethanol Production Using Saccharide-Containing Permeate-Product 750 mL of saccharide-containing permeate-product was inoculated with 50 mL inoculate of *Saccharomyces cerivisiae* resulting in a start optical density of 1.8. The fermentation medium was stirred with 400 rpm at pH 4.5 and 32° C. using a Multifors® lab fermenter (Infors®, Switzerland). After 70.5 hours the fermentation was stopped. Samples were subsequently applied to HPLC and GC analysis. The results show that glucose as well as fructose were completely consumed and 65 g/L Ethanol produced.

What is claimed is:
1. A process for the hydrolysis of biomass comprising:
   a) Contacting the biomass with an enzyme-composition containing at least one enzyme selected from the class of hydrolases in a vessel;
   b) Eliminating at least part of said biomass;
   c) Subjecting said at least part of said biomass to a filtration and removing the permeate; and
   d) Backfeeding of at least part of the filtrated biomass to the vessel;
   wherein step b) is carried out in an outer circuit;
   wherein step c) is carried out in an inner circuit;
   wherein said outer circuit and said inner circuit are different;
   wherein the outer circuit is in closer proximity to step a) than the inner circuit;
   wherein filtration is carried out by use of at least one filtration module comprising at least one ceramic membrane;
   wherein dry matter content of the biomass is from 5 to 40 wt.-%;
   wherein each circuit is equipped with a pump; and
   wherein at least two of steps a) to d) are carried out simultaneously; and
   wherein after step d), the filtrated biomass that is not backfed to the vessel is circulated back to the at least one filtration module.
2. The process according to claim 1, wherein the enzyme-composition contains cellulases, hemicellulases and/or pectinases.

3. The process according to claim 2, wherein the enzyme-composition further contains at least one enzyme selected from pectinmethylesterases, rhamnogalacturonases, 1,3-/1,6-beta-D-glucanases and xylanases.

4. The process according to claim 1, wherein the biomass is selected from cellulose, hemicellulose and/or lignin-containing biomass.

5. The process according to claim 4, wherein the biomass is selected from sugar-beet, sugar-cane, straw, corn, wood, oilseed and mixtures thereof.

6. The process according to claim 1, further comprising:
  e) adding an amount of liquid corresponding to the amount removed by filtration according to step c).

7. The process according to claim 6, further comprising:
  f) Adding an amount of fresh biomass.

8. The process according to claim 7, wherein steps b) to e) or b) to f) are repeated at least once.

9. The process according to claim 6, wherein each of steps a) to e) are carried out simultaneously.

10. The process according to claim 1, wherein dry matter content of the biomass is from 15 to 30 wt.-%.

11. The process according to claim 1, wherein dry matter content of the biomass is 22 wt.-%.

* * * * *